US00PP26498P3

(12) United States Plant Patent
Sproul

(10) Patent No.: US PP26,498 P3
(45) Date of Patent: Mar. 15, 2016

(54) SHRUB ROSE PLANT NAMED 'SPROLYCH'

(50) Latin Name: *Rosa hybrida*
Varietal Denomination: Sprolych

(71) Applicant: CP DELAWARE, INC., Wilmington, DE (US)

(72) Inventor: James A. Sproul, Bakersfield, CA (US)

(73) Assignee: CP DELAWARE, INC., Wilmington, DE (US)

( * ) Notice: Subject to any disclaimer, the term of this patent is extended or adjusted under 35 U.S.C. 154(b) by 117 days.

(21) Appl. No.: 13/998,618

(22) Filed: Nov. 18, 2013

(65) Prior Publication Data

US 2015/0143589 P1 May 21, 2015

(51) Int. Cl.
*A01H 5/02* (2006.01)

(52) U.S. Cl.
USPC ..... Plt./103

(58) Field of Classification Search
USPC ..... Plt./103
See application file for complete search history.

*Primary Examiner* — Keith Robinson
(74) *Attorney, Agent, or Firm* — Buchanan, Ingersoll & Rooney PC

(57) ABSTRACT

A new and distinct variety of shrub rose plant is provided which forms in abundance on a substantially continuous basis attractive semi-double ivory cream blossoms that possess a substantially non-fading blotch of deep burgundy at the center of the petals. The vegetation is vigorous and strong and the growth habit is compact and bushy. Attractive ornamental semi-glossy dark green foliage is formed. The plant is particularly well suited for growing in a Western landscape. Distinctive ornamentation is provided.

1 Drawing Sheet

Botanical/commercial classification: *Rosa hybrida*/Shrub Rose Plant.

Varietal denomination: cv. Sprolych.

SUMMARY OF THE INVENTION

The new variety of landscape shrub rose plant of the present invention was created by artificial pollination carried out at Bakersfield, Calif., U.S.A., wherein two parents were crossed which previously had been studied in the hope that they would contribute the desired characteristics. Each parent was not patented and possessed a complex parentage as indicated hereafter. More specifically, the parentage can be summarized as follows: {[('Orangeade'×'Auscot')×Wekfabpur']×('Geisha'×'Scrivluv')}×mixed Hulthemia pollen. The 'Auscot' variety is marketed under the ABRAHAM DARBY trademark and is the subject of U.S. Plant Pat. No. 7,215. The 'Wekfabpur' variety is marketed under the MIDNIGHT BLUE trademark and is the subject of U.S. Plant Pat. No. 16,623. The 'Scrivluv' variety is marketed under the BABY LOVE trademark and is non-patented in the United States. The 'Orangeade' and 'Geisha' varieties are non-patented in the United States.

The seeds resulting from the above pollination were sown and small plants were obtained which were physically and biologically different from each other. Selective study resulted in the identification of a single plant of the new variety.

It was found that the new variety of landscape shrub rose plant of the present invention possesses the following combination of characteristics:

(a) abundantly and substantially continuously forms attractive semi-double ivory cream blossoms that possess a substantially non-fading blotch of deep burgundy at the center of the petals, (b) exhibits a compact and bushy growth habit, (c) forms vigorous and strong vegetation, (d) forms attractive ornamental dark green foliage with a semi-glossy finish on the upper surface, and (e) is well suited for providing distinctive ornamentation.

A new rose variety is provided having attractive multicolored blossoms, combined with substantially continuous blooming. The plant reblooms well and displays an attractive compact growth habit.

The new variety well meets the needs of the horticultural industry particularly when grown in a Western landscape. It can be grown to advantage as attractive ornamentation in parks, gardens, public areas, and residential landscapes. The ivory cream and burgundy blossom coloration contrasts nicely with the dark green foliage.

The new variety can be readily distinguished from the 'Sprolem' variety (U.S. Plant Pat. No. 23,580), as well as plants in its ancestry. More specifically, the 'Sprolem' variety displays dissimilar bright yellow blossoms and a considerably larger growth habit. The 'Orangeade' variety displays blossoms that are clear orange in coloration. The 'Auscot' variety forms very large very double yellow blossoms with dark pink at the base. The 'Wekfabpur' variety forms purple blossoms with a lighter under surface. The 'Geisha' variety displays mauve blossoms. The 'Scrivluv' variety displays single deep yellow blossoms. It further is recognized that Hulthemia roses generally bloom only once a year and generally display an unattractive growth habit.

The characteristics of the new variety have been found to be homogeneous and stable and are strictly transmissible by asexual propagation by the use of stem cuttings from one generation to another at Wasco, Calif., U.S.A. Accordingly, the new variety can be asexually reproduced in a true-to-type manner. After approximately 10 days root formation is readily apparent on stem cuttings.

The new variety has been named 'Sprolych', and will be marketed under the EYECONIC and LYCHEE LEMONADE trademarks.

BRIEF DESCRIPTION OF THE PHOTOGRAPHS

The accompanying photographs show, as nearly true as it is reasonably possible to make the same in a color illustrations of this character, typical specimens of the new variety. The illustrated plants were approximately one year of age and was growing outdoors in the field on their own roots at Davis, Calif., U.S.A.

DETAILED BOTANICAL DESCRIPTION

Figure 1:
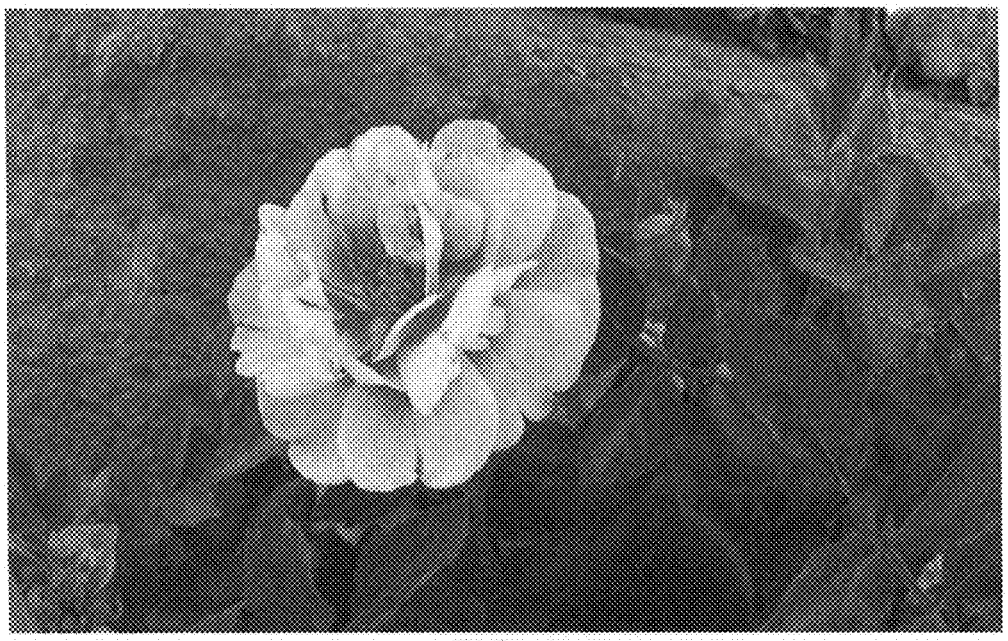
FIG. 1 illustrates a close view of a typical blossom and foliage of the new variety. The attractive ivory cream and burgundy coloration of a typical semi-double blossom is shown.
Figure 2:
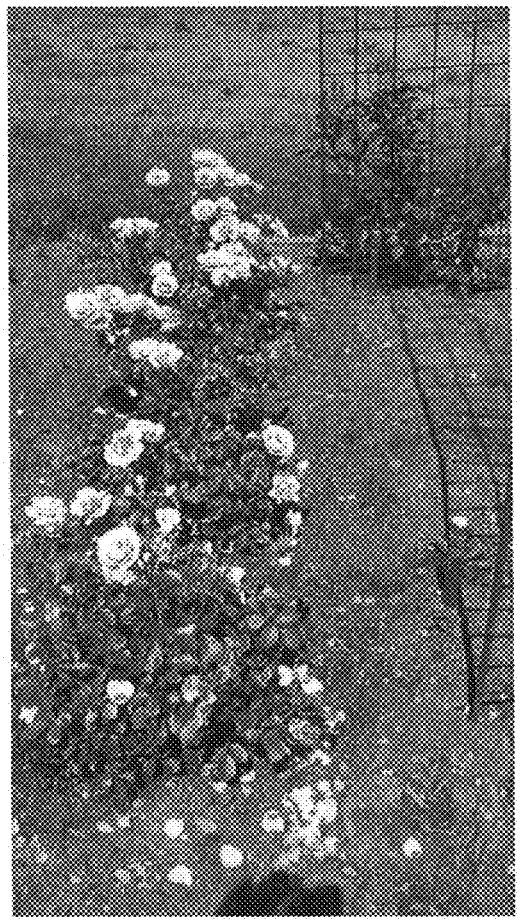
FIG. 2 illustrates a row of flowering plants of the new variety wherein the compact and bushy growth habit is shown.

The chart used in the identification of colors is that of The Royal Horticultural Society (R.H.S. Colour Chart-1995 Edition). The description is based on the observation of two-year-old specimens of the new variety during September while growing outdoors on their own roots at West Grove, Pa., U.S.A.

Class: Shrub Rose.

Plant:

*Height*.—Approximately 45 cm on average when mature.

*Width*.—Approximately 45 cm on average when mature.

*Habit*.—Compact and bushy.

*Roots*.—Fibrous network, and near Greyed-Orange Group 164D in coloration.

Branches:

*Number*.—Commonly display 2 or 3 main branches on average.

*Length*.—Commonly approximately 55 to 63 cm on average.

*Diameter*.—Commonly approximately 1 to 3 cm on average.

*Color*.—Young stems: near Green Group 143A. Adult wood: near Green Group 137B overlaid with Grey-Brown Group 199A.

*Texture*.—Young stems: generally smooth with thorns. Adult wood: somewhat rough.

*Thorns*.—Size on young stems: approximately 5 cm in length on average, and on mature wood approximately 7 cm in length on average. Texture: generally smooth. Quantity: commonly observed to be present in a moderate quantity. Color on young stems: near Yellow-Green Group 144A. Color on mature wood: near Grey-Brown Group 199A.

Leaves:

*Arrangement*.—Odd — pinnate.

*Size*.—A five-leaflet leaf commonly is approximately 6.7 cm in length on average, and approximately 6 cm in width on average.

*Apex*.—Acute.

*Base*.—Broadly cuneate.

*Leaflets*.—Number: 3, 5, and 7. Shape: broadly ovate with a serrate margin. Texture (upper surface): smooth and semi-glossy. Texture (under surface): smooth. Size: terminal leaflets commonly are approximately 4.6 cm in length on average and approximately 3.3 cm in width on average, and lower leaflets commonly are approximately 2 cm in length on average and approximately 1.6 cm in width on average. Color (young foliage): on the upper surface near Green Group 143C and on the under surface near Yellow-Green Group 144A. Color (fully mature foliage): on the upper surface near Green Group 139A, and on the under surface near Green Group 137A.

*Venation*.—Pinnate.

*Vein color*.—Near Yellow-Green Group 146B on the upper surface and near Yellow-Green Group 145A on the under surface.

*Stipules*.—Commonly rough on the upper surface and smooth on the under surface.

*Petioles*.—Length: commonly approximately 1 cm on average. Diameter: commonly approximately 1 mm on average. Color: near Yellow-Green Group 146C. Texture: commonly rough on the upper surface and smooth on the lower surface. Strength: relatively strong.

*Rachis*.—Length: commonly approximately 1.5 cm on average. Diameter: commonly approximately 1 mm on average. Color: near Yellow-Green Group 146C. Texture: commonly rough on the upper surface and smooth on the lower surface. Strength: relatively strong.

Inflorescence:

*Number of flowers*.—Singly or in cluster of two or three blossoms per stem, and commonly approximately 24 flowers on plant at a given time.

*Peduncle*.—Relatively strong, covered with small flexible thorns less than 1 mm in length, near Yellow-Green Group 144A in coloration, approximately 4.5 cm in length on average, and approximately 2 mm in diameter.

*Sepals*.—Number: five. Length: commonly approximately 2.3 cm on average. Width: commonly approximately 8 mm on average at the widest point. Upper surface: somewhat rough and covered with short hairs. Under surface: smooth.

*Buds*.—Shape: ovoid. Length: approximately 1.5 cm on average. Diameter: commonly approximately 1.1 cm on average. Texture: smooth. Color: near Yellow Group 11A when opening.

*Flower*.—Form: semi-double, cuplike. Diameter: approximately 6 cm on average. Color (when opening begins): Upper surface: near Yellow-Orange Group 19C overlaid with near Red-Purple Group 63D transitioning at the center to near Red-Purple Group 61B, and finally to Yellow Group 11A at the point of attachment. Under surface: near Yellow Group 11C with near Yellow Group 12B at the point of attachment. Color (when fully open): Upper surface: near Yellow Group 11D transitioning at the center to near Red-Purple Group 67B, subsequently to near Red-Purple Group 65D, and finally to near Yellow Group 4D at the point of attachment. Under surface: near Yellow Group 11A throughout. Fragrance: slight. Petal shape: obcordate. Petal length: commonly approximately 3.1 cm on average. Petal width: commonly approximately 3.3 cm on average. Petal margin:

entire. Petal apex: broadly obcordate. Petal base: broadly cuneate. Petal number: approximately 15 on average. Petal drop: good, with the petals commonly dropping cleanly and freely. Stamen number: approximately 90 on average. Anthers: near Yellow-Orange Group 14A in coloration. Filaments: near Yellow-Orange Group 18C, and approximately 1 cm in length on average. Pollen: commonly formed in a sparse amount, and near Yellow Group 11A in coloration. Pistils: separate and free, and commonly approximately 35 in number on average. Stigmas: near Yellow-Orange Group 19C in coloration, and approximately 1 mm in diameter. Petaloid number: commonly approximately 3 or 4 on average. Petaloid size: commonly approximately 1.7 cm in length on average, and approximately 1 cm in width on average. Petaloid color: commonly near Yellow Group 4D at the point of attachment, then transitioning to near Red-Purple Group 65D, then to near Red-Purple Group 67B, and finally to near Yellow Group 11D at the apex. Receptacle: smooth, generally circular in shape, achenes stand on the bottom and wall, approximately 6 mm in diameter on average, and near Yellow-Green Group 144A in coloration.

*Sepals*.—Commonly near Green Group 139C on the upper surface and near Yellow-Green Group 144A on the lower surface.

Development:

*Vegetation*.—Vigorous and strong.

*Blossoming*.—Abundant and substantially continuous.

*Resistance to diseases*.—*Diplocarpon rosae* (Blackspot), *Podosphaera pannosa* (Powdery Mildew), and *Phragmidium tuberculatum* (Rust) typical for the type (Hulthemia).

*Propensity to form hips/seeds*.—None observed during observations to date.

*Hardiness*.—To at least U.S.D.A Hardiness Zone No. 6.

Plants of the new 'Sprolych' variety have not been observed under all possible environmental conditions to date. Accordingly, it is possible that the phenotypic expression may vary somewhat with changes in light intensity and duration, cultural practices, and other environmental conditions.

I claim:

1. A new and distinct variety of shrub rose plant characterized by the following combination of characteristics:

(a) abundantly and substantially continuously forms attractive semi-double ivory cream blossoms that possess a substantially non-fading blotch of deep burgundy at the center of the petals, (b) exhibits a compact and bushy growth habit, (c) forms vigorous and strong vegetation, (d) forms attractive ornamental dark green foliage with a semi-glossy finish on the upper surface, and (e) is well suited for providing distinctive ornamentation; substantially as herein shown and described.

* * * * *